US011116879B2

(12) United States Patent
Nobis et al.

(10) Patent No.: US 11,116,879 B2
(45) Date of Patent: Sep. 14, 2021

(54) SURGICAL TOOL WITH FLUID CONTROL PATHWAYS

(71) Applicant: Ethicon LLC, Guaynabo, PR (US)

(72) Inventors: Rudolph H. Nobis, Mason, OH (US); Patrick J. Minnelli, Harrison, OH (US); Kevin M. Montgomery, Camden, OH (US)

(73) Assignee: Cilag GmbH International, Zug (CH)

( * ) Notice: Subject to any disclaimer, the term of this patent is extended or adjusted under 35 U.S.C. 154(b) by 396 days.

(21) Appl. No.: 15/666,120

(22) Filed: Aug. 1, 2017

(65) Prior Publication Data

US 2019/0038816 A1   Feb. 7, 2019

(51) Int. Cl.
*A61M 1/00* (2006.01)
*A61M 3/02* (2006.01)

(52) U.S. Cl.
CPC ........ *A61M 1/0058* (2013.01); *A61M 1/0062* (2013.01); *A61M 1/774* (2021.05); *A61M 1/83* (2021.05); *A61M 3/022* (2014.02); *A61M 3/0254* (2013.01); *A61M 1/85* (2021.05); *A61M 2205/3334* (2013.01)

(58) Field of Classification Search
CPC .. A61M 1/0058; A61M 3/022; A61M 1/0062; A61M 1/0064; A61M 1/0078; A61M 3/0254; A61M 1/0084; A61M 1/0023; A61M 3/0283; A61M 2205/3334; A61M 39/225; A61M 39/223; A61M 2039/224; A61M 2039/226; A61M 1/774; A61M 1/83; A61M 1/85; F16K 3/26
See application file for complete search history.

(56) References Cited

U.S. PATENT DOCUMENTS

| 5,395,312 A * | 3/1995 | Desai ............... A61B 17/00234 |
| | | 604/152 |
| 6,375,653 B1 * | 4/2002 | Desai ............... A61B 17/00234 |
| | | 604/131 |
| 6,419,654 B1 * | 7/2002 | Kadan ................ A61B 1/00068 |
| | | 600/101 |

(Continued)

FOREIGN PATENT DOCUMENTS

WO    WO-94008525 A1    4/1994

OTHER PUBLICATIONS

International Preliminary Report on Patentability for PCT App. PCT/IB2018/055738 dated Feb. 4, 2020.

*Primary Examiner* — Theodore J Stigell
(74) *Attorney, Agent, or Firm* — Mintz Levin Cohn Ferris Glovsky and Popeo, P.C.

(57) ABSTRACT

Surgical tools are provided herein that are configured to apply suction and irrigation at a surgical site during the course of a surgical procedure. A surgical tool can include a handle that has a suction flow path configured to provide suction therethrough and an irrigation flow path configured to provide irrigation therethrough. The suction flow path and the irrigation flow path can share a common path along at least partial lengths thereof. An elongate shaft can extend distally from the handle and can have an inner lumen that is in communication with the suction flow path and the irrigation flow path. The inner lumen can thus be configured to provide suction from the suction flow path to a surgical site to remove matter therefrom and to provide irrigation from the irrigation flow path to the surgical site to provide fluid thereto.

18 Claims, 8 Drawing Sheets

(56) References Cited

U.S. PATENT DOCUMENTS

| | | | |
|---|---|---|---|
| 2003/0120203 A1* | 6/2003 | Guo | A61M 1/0064 |
| | | | 604/35 |
| 2015/0025311 A1* | 1/2015 | Kadan | A61B 1/015 |
| | | | 600/104 |
| 2016/0135872 A1 | 5/2016 | Minnelli et al. | |
| 2018/0161483 A1* | 6/2018 | Chuang | A61M 3/0283 |
| 2018/0229021 A1* | 8/2018 | Donlon | A61B 34/35 |
| 2019/0059980 A1* | 2/2019 | Shelton, IV | A61B 18/1206 |

* cited by examiner

SURGICAL TOOL WITH FLUID CONTROL PATHWAYS

FIELD

The present invention relates generally to surgical tools for controlling irrigation and suction at surgical sites and methods for using the same.

BACKGROUND

Surgical tools are used in various open, endoscopic, and laparoscopic surgeries to transect or coagulate tissue or artifacts at a surgical site. During such operations, a surgeon may desire to apply irrigation and/or suction at the surgical site, for example to clean the site or to clear tissue, debris, fluid, and/or artifacts. Performing irrigation and suction through a single surgical tool provides an easier experience for a surgeon, especially when the surgeon is attempting to transect or coagulate tissue. However, existing surgical tools struggle to successfully deliver irrigation and suction to a surgical site without experiencing some level of clogging and/or malfunctioning because irrigation and suction pathways through such surgical tools are often narrow, curving, and positioned adjacent to one another, for example leading to clogging while attempting suction without a simple way to clear a clog or restore fluid flow and suction through the tool. This can increase surgical times and frustrate a surgeon.

Accordingly, there remains a need for improved surgical tools and methods for controlling irrigation and suction at surgical sites.

SUMMARY

In general, surgical tools for controlling irrigation and suction at surgical sites and methods for using the same are provided herein.

In one aspect, a surgical device is provided that in one embodiment includes a handle and an elongate shaft. The handle has a first chamber, a second chamber, and an opening therebetween. The handle has a suction flow path configured to provide suction therethrough and an irrigation flow path configured to provide irrigation therethrough. The suction flow path and the irrigation flow path share a common path through the first chamber, the opening, and the second chamber thereof. The elongate shaft extends distally from the handle and has an inner lumen extending therethrough. The inner lumen is in communication with the suction flow path such that the inner lumen is configured to provide suction therethrough to allow matter to enter an open distal end of the shaft. The inner lumen is in communication with the irrigation flow path such that the inner lumen is configured to provide irrigation therethrough to allow fluid to exit the open distal end of the shaft.

The device can vary in any number of ways. For example, the device can include an actuator configured to be selectively actuated to cause the suction to be provided through the suction flow path and to cause the irrigation to be provided through the irrigation flow path. In another example, the suction flow path and the irrigation flow path can share a common opening between a distal end of the handle and a proximal end of the shaft. In still another example, the device can include a first valve that biases the suction flow path closed and a second valve that biases the irrigation flow path closed. In at least some embodiments, the device can also include a first actuator configured to be actuated to counteract the bias of the first valve to allow the suction to be provided through the suction flow path, and a second actuator configured to be actuated to counteract the bias of the second valve to allow the irrigation to be provided through the irrigation flow path. In another example, the shaft can have a longitudinal axis, and the first and second valves can be positioned along the longitudinal axis of the shaft. In yet another example, the second valve can be positioned distally relative to the first valve along the longitudinal axis.

In another example, the shaft can have a first longitudinal axis, and the common path can have a second longitudinal axis that is substantially coaxial with the first longitudinal axis. In at least some embodiments, each of the irrigation and suction flow paths can have a length proximal to a proximal end of the common path that is at an angular offset from the second longitudinal axis.

In yet another example, the suction flow path can couple to a suction port on the handle and the irrigation flow path can couple to an irrigation port on the handle. In at least some embodiments, the suction port can be larger than the irrigation port. In at least some embodiments, the suction flow path can extend distally from the suction port for a first length before reaching the common path, and the irrigation flow path can extend distally from the irrigation port for a second length before reaching the common path.

In another example, the suction flow path can have a length proximal to a proximal end of the common path that is configured to have a velocity greater than a velocity of the suction flow path in the common path.

In another embodiment, a surgical device is provided that includes an end effector, a cannulated shaft, and a handle. The cannulated shaft has a proximal end and a distal end, and the end effector is disposed on the distal end thereof. The shaft is configured to provide suction and irrigation to a surgical site. The handle is coupled to the proximal end of the shaft and has a distal end and a proximal end. The handle has a suction pathway configured for providing suction to the shaft and an irrigation pathway configured for providing irrigation to the shaft, and the handle has a shared opening positioned proximally from the distal end of the handle and a shared chamber directly engaged with and positioned proximally from the shared opening. The shared opening and the shared chamber have both the suction pathway and the irrigation pathway pass therethrough such that the suction pathway and the irrigation pathway have a shared distal portion in the handle and extend along a central linear axis of the handle.

The device can have any number of variations. For example, the suction pathway can couple to a suction port on the handle, and the irrigation pathway can couple to an irrigation port on the handle, and the suction port can be larger than the irrigation port. In another example, the handle can include an irrigation actuator configured to actuate the irrigation pathway and a suction actuator configured to actuate the suction pathway. In still another example, only one of the irrigation pathway and the suction pathway can be active at a time. In another example, the irrigation pathway and the suction pathway can be configured to be active simultaneously. In yet another example, the suction pathway and the irrigation pathway can have a shared distal portion in the handle and extend along a central linear axis of the handle. In another example, the suction pathway and the irrigation pathway can extend from the distal end of the handle to the proximal end of the handle. In still another example, the shaft can be configured to rotate about an elongated axis thereof.

In another aspect, a surgical method is provided that in one embodiment includes advancing a distal end of a surgical device into a body of a patient. The surgical device has a handle and a shaft extending distally therefrom, and the handle has a shared opening positioned proximally from a distal end of the handle and a shared chamber directly engaged with and positioned proximally from the shared opening. The method also includes selectively applying suction to a surgical site through a suction pathway that extends through the surgical device and applying irrigation to the surgical site through an irrigation pathway that extends through the handle of the surgical device. The suction pathway and the irrigation pathway have independent proximal portions in the surgical device and have a shared distal portion at least through the shared opening and the shared chamber in the surgical device.

The method can have any number of variations. For example, applying the suction can cause a first valve positioned along a longitudinal axis of the handle and biasing the suction pathway closed to open, and applying the irrigation can cause a second valve positioned along the longitudinal axis of the handle distal to the first valve and biasing the irrigation pathway closed to open. In another example, the surgical device can be configured to provide only one of suction and irrigation at a time. In still another example, the method can include delivering energy to the surgical site with the surgical device.

BRIEF DESCRIPTION OF DRAWINGS

The embodiments described above will be more fully understood from the following detailed description taken in conjunction with the accompanying drawings. The drawings are not intended to be drawn to scale. For purposes of clarity, not every component may be labeled in every drawing. In the drawings.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed devices and methods, such dimensions are not intended to limit the types of shapes that can be used in conjunction with such devices and methods. A person skilled in the art will recognize that an equivalent to such linear and circular dimensions can easily be determined for any geometric shape. Sizes and shapes of the devices, and the components thereof, can depend at least on the anatomy of the subject in which the devices will be used, the size and shape of components with which the devices will be used, and the methods and procedures in which the devices will be used.

In general, surgical tools are provided herein that are configured to apply suction and irrigation at a surgical site during the course of a surgical procedure. A surgical tool can include a handle that has therein a suction flow path configured to provide suction therethrough and an irrigation flow path configured to provide irrigation therethrough. The suction flow path and the irrigation flow path can share a common path along at least a partial length of the handle. An elongate shaft can extend distally from the handle and can have an inner lumen that is in communication with the suction flow path and the irrigation flow path. The inner lumen can thus be configured to provide suction from the suction flow path to a surgical site to remove matter therefrom and to provide irrigation from the irrigation flow path to the surgical site to provide fluid thereto, such as saline, water, etc. Irrigation and suction may be easily provided at a surgical site without using multiple devices and with less clogging or malfunctioning than typical devices, e.g., because of the shared common path of the suction and irrigation flow paths. If a clog or malfunction does occur, suction and irrigation can be alternated between the suction and irrigation flow paths to clear any obstruction and allow free flow of matter and fluid along the flow paths. The shared common path can also be straighter than typical devices, avoiding curves or edges that can cause clogs or disrupt flow.

Figure 1:
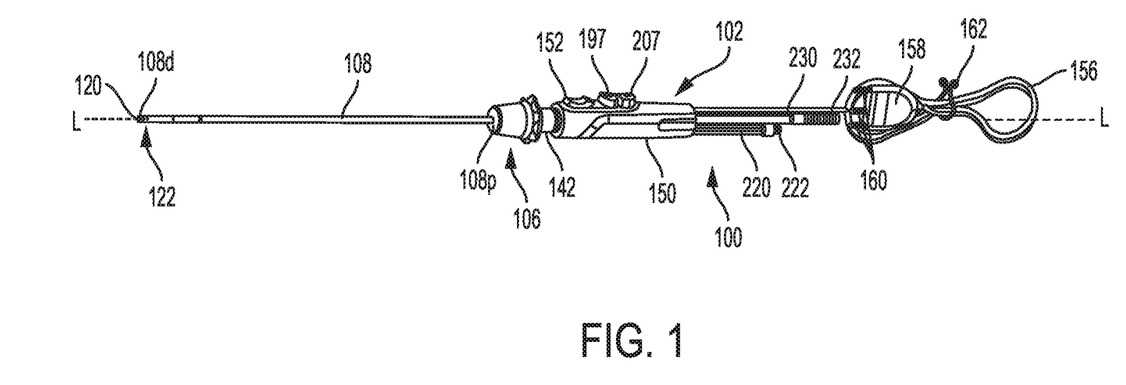
FIG. 1 is a perspective view of a surgical device for applying irritation and suction.
Figure 2:
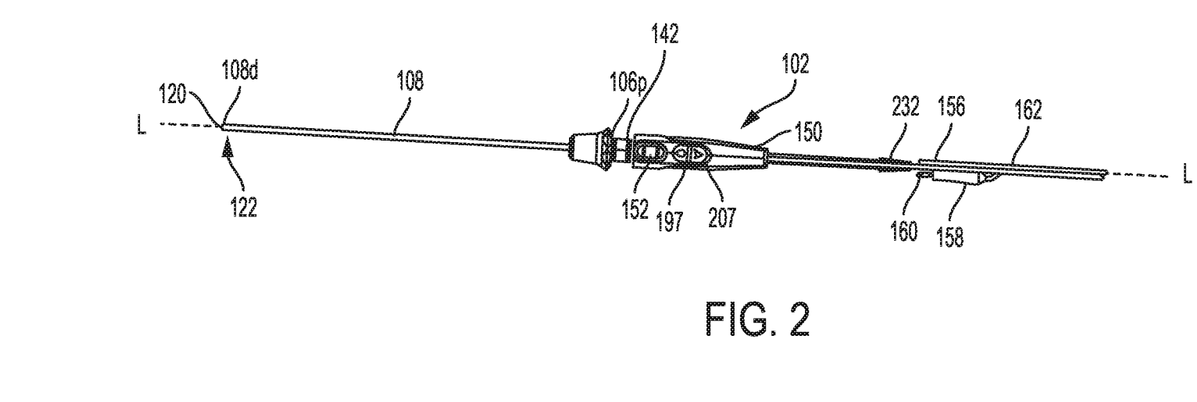
FIG. 2 is a top view of the surgical device of FIG. 1.

FIGS. 1 and 2 illustrate an embodiment of a surgical device 100 configured to provide irrigation and suction to a surgical site. As illustrated in FIGS. 1-4, the device 100 includes a handle 102, an elongate shaft 104, a knob 106, and an outer sheath 108. The knob 106 is positioned at a distal end of the handle 102. The shaft 104 is positioned within the outer sheath 108, and the shaft 104 and the outer sheath 108 extend distally from the handle 102 and the knob 106. A proximal end 104p of the shaft 104 is coupled to the handle 102, and a proximal end 108p of the sheath 108 is coupled to the knob 106. Distal ends 104d, 108d of the shaft 104 and the outer sheath 108 are configured to be advanced into a patient's body during a surgical procedure.

The knob 106 is configured to translate both away from and towards the handle 102 along a longitudinal axis L of the outer sheath 108 such that, as the knob 106 advances distally away from the handle 106, the outer sheath 108 correspondingly advances distally. The handle 102 and the shaft 104 are configured to remain stationary with respect to the knob 106 and the outer sheath 108, so the distal end 108d of the outer sheath 108 can be configured to extend over a distal end 104d of the shaft 104 when the knob 106 advances distally to an extended position. Similarly, as the knob 106 retracts proximally towards the handle 102, the outer sheath 108 correspondingly moves proximally. Thus, retraction of the knob 106, e.g. proximal movement, is configured to cause the outer sheath 108 to move proximally to expose the distal end 104d of the shaft 104. In at least some embodiments, an end effector can be positioned at the distal end 104d of the shaft 104 and be configured to perform a variety of functions, such as to transect tissue, coagulate tissue, etc.

Figure 3:
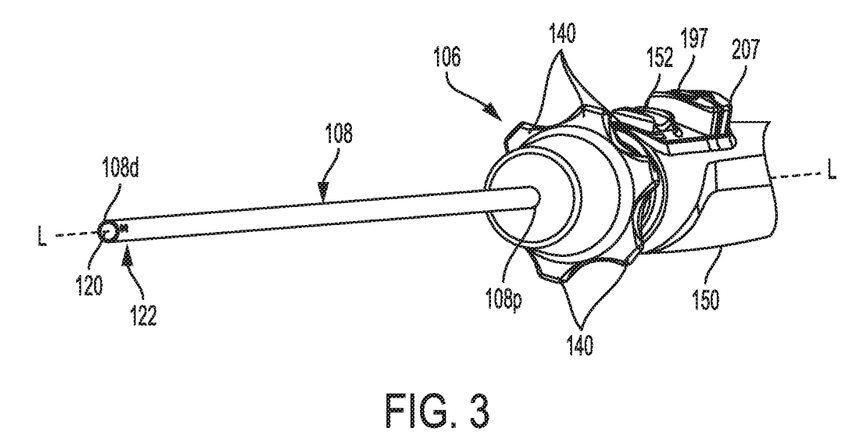
FIG. 3 is a perspective view of a distal portion of the surgical device of FIG. 1.
Figure 4:
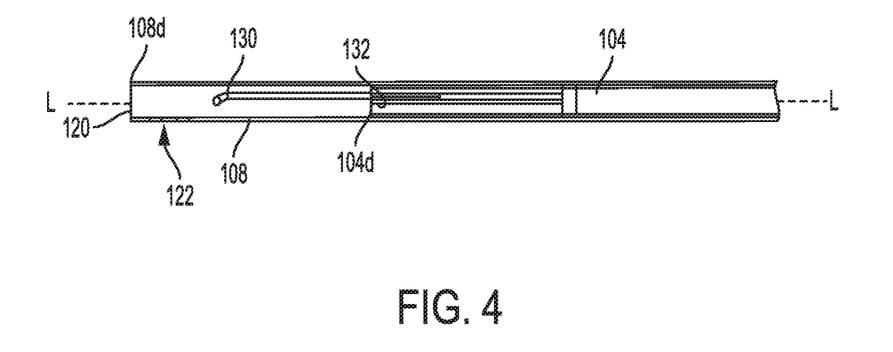
FIG. 4 is a cross-sectional side view of a distal portion of the surgical device of FIG. 3.

As illustrated in FIGS. 3 and 4, the outer sheath 108 can be a cannulated, elongate cylindrical tube. An opening 120 is formed at the distal end 108d of the outer sheath 108. The proximal end 108p of the outer sheath 108 can be configured to couple to the knob 106 through any of a number of different techniques, such as an interference fit, a snap-fit, and a threaded configuration. In some embodiments, engagement between the outer sheath 108 and the knob 106 can be configured to allow the outer sheath 108 to be removably and replaceably coupled to the knob 106, thereby allowing sheaths of various sizes, shapes, and configurations to be selectively attached to the device 100. The outer sheath 108 can include a plurality of holes 122 formed through an outer surface thereof. The holes 122 can be configured to be in fluid communication with an inner passageway extending through the sheath 108 and also in fluid communication with an inner passageway extending through the shaft 104. The holes 122 are configured to apply suction and/or irrigation therethrough. In at least some embodiments, the 122 holes can be configured to vent and facilitate suction and irrigation if the distal end 108d of the sheath 108 becomes clogged. Any number of holes 122 can be formed, such as a number between zero holes and ten holes. Fluid and suction forces can be provided through the opening 120 of the outer sheath 108, for example when no holes are formed in the outer sheath 108 or in addition to forces through the one or more holes 122. In some embodiments, the outer sheath 108 can be excluded entirely.

The elongate shaft 104 includes a cannulated, elongate cylindrical tube disposed within the outer sheath 108. The shaft 104 includes an opening 132 at the distal end 104d positioned proximal to the distal end 108d of the outer sheath 108, as shown in FIG. 4, such that the shaft's distal end 104d can be selectively covered by and exposed by the outer sheath 108. The shaft 104 can be configured to receive therein fluid and/or a suction force. For example, a fluid source and/or a suction source can be disposed in the handle 102 or disposed outside of the handle 102 and connected to the handle 102 such that a fluid or a suction force can be supplied through the elongate shaft 104, through the outer sheath 108, and out of the device 100 to a surgical site. In at least some embodiments, the proximal end 104p of the shaft 104 can be in electrical communication with components in the handle 102 such that energy can be delivered through the shaft 104 to an end effector positioned at the distal end 104d of the shaft 104. In the illustrated embodiment, an end effector 130 at the shaft's distal end 104d is monopolar such that energy delivered travels from the end effector 130, to tissue being treated, and then returns through a monopolar ground plate attached to the patient to complete the path. In other embodiments, the end effector can be bipolar so that energy supplied to one electrode can pass from the electrode, through the tissue, and to a second, return electrode. Various other end effectors can also be provided, as mentioned above. In at least some embodiments, the end effector can be removable and replaceable on the device 100.

Figure 5:
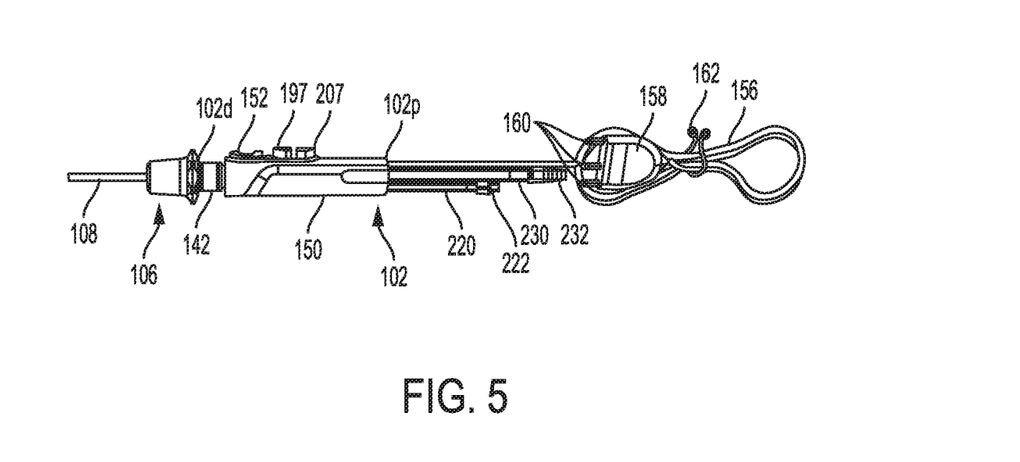
FIG. 5 is a side view of a proximal portion of the surgical device of FIG. 1.
Figure 6:
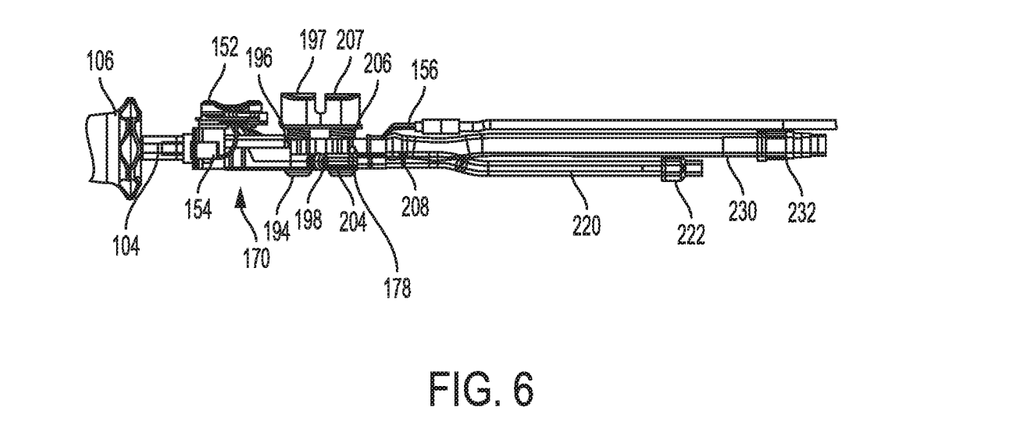
FIG. 6 is a side view of a handle of the surgical device of FIG. 1 with a housing removed.
Figure 7:
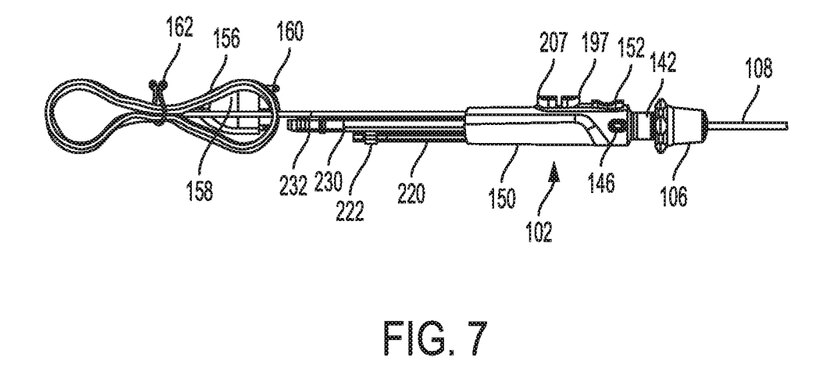
FIG. 7 is another side view of a proximal portion of the surgical device of FIG. 1.
Figure 8:
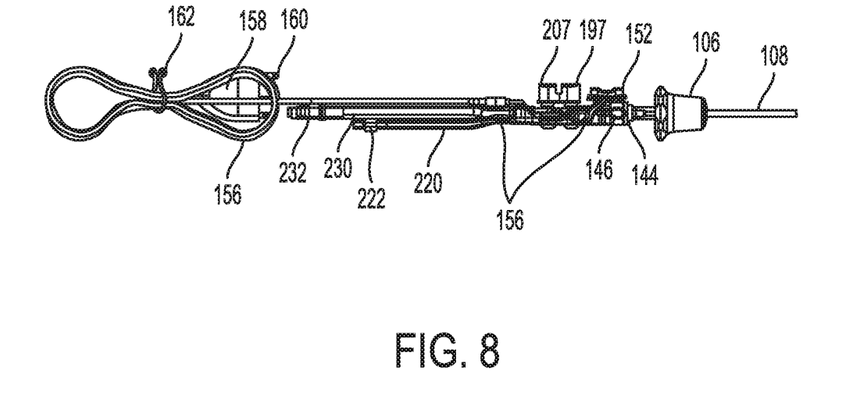
FIG. 8 is a side view of the proximal portion of FIG. 7 with a housing removed.
Figure 9:
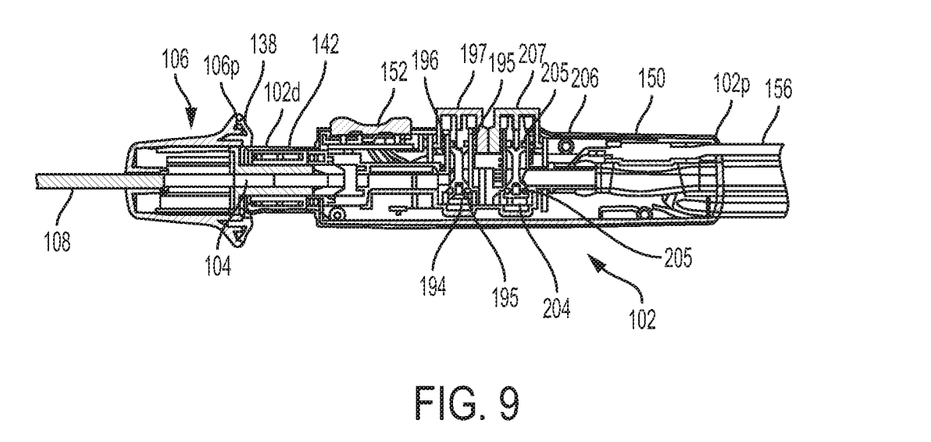
FIG. 9 is a cross-sectional side view of a handle of the surgical device of FIG. 1.

The knob 106 in this illustrated embodiment is a generally cylindrical member and has an opening or bore extending therethrough through which the elongate shaft 104 extends to couple to the handle 102, as illustrated in FIGS. 5 and 9. A central longitudinal axis of the knob 106 is shared with the central longitudinal axis L of the outer sheath 108. The knob 106 can include a mating feature that is complementary to a mating feature on the outer sheath 108 to mate together the knob 106 and the sheath 108, such as by interference fit. A plurality of engagement members 140 can be formed on the knob 106 to assist a user in gripping and manipulating the knob 106. The engagement members 140 can have a variety of forms, such as ridges, bumps, grooves, pegs, etc. A proximal end 106p of the knob 106 can be sized and shaped to receive a distal portion 142 of the handle 102 therein, thus allowing the knob 106 to translate along the distal portion 142 of the handle 102 such that the distal end 104d of the elongate shaft 104 can be exposed by the outer sheath 108. The knob 106 can have a circular spring member 138 positioned along the proximal end 106p of the knob 106 that is configured to bias the knob 106 distally such that the outer sheath 108 covers the distal end 104d of the shaft 104 when no force is being applied to the knob 106. The knob 106 can be configured to freely rotate about the longitudinal axis L in both the clockwise and counterclockwise directions, causing corresponding rotation of the outer sheath 108, as in this illustrated embodiment.

The handle 102 has a generally cylindrical shape. However, a variety of other shapes can be used for the handle 102. As illustrated in FIGS. 5-9, the handle 102 includes a housing 150 including the distal portion 142 along which the knob 106 is configured to translate. In at least some embodiments, the distal portion 142 can include a catch or lock 144 configured to prevent the knob 106 from moving distally when the knob 106 has been translated proximally along the distal portion 142 of the handle 102, and the handle 102 can include a release mechanism 146, e.g., a button (as in this illustrated embodiment), lever, switch, etc. disposed on a side of the housing 150, that is configured to be actuated to release or unlock the knob 106 and thereby allow the knob 106 to move distally. The handle 102 can include components configured to apply energy to the end effector 130 and components configured to provide irrigation and/or suction through the shaft 104 and the outer sheath 108. For example, an actuator, in the form of a button 152 in this illustrated embodiment, is disposed on the housing 150 and is electrically coupled to circuitry 154 configured to deliver energy to the end effector 130 in response to actuation (e.g. pushing) of the button 152 and is electrically coupled to cables 156 that extend proximally from the handle 102 and terminate in a yoke 158 and plugs 160 configured to be coupled to a power device (not shown). The cables 156 can be clipped together with a clip 162 to, e.g., facilitate storage. The button 152 can be configured to be actuated to close a circuit to delivery energy to the end effector 130 through the cables 156. A variety of different configurations can be used in other embodiments, however, including removing electrical components entirely.

Figure 14:
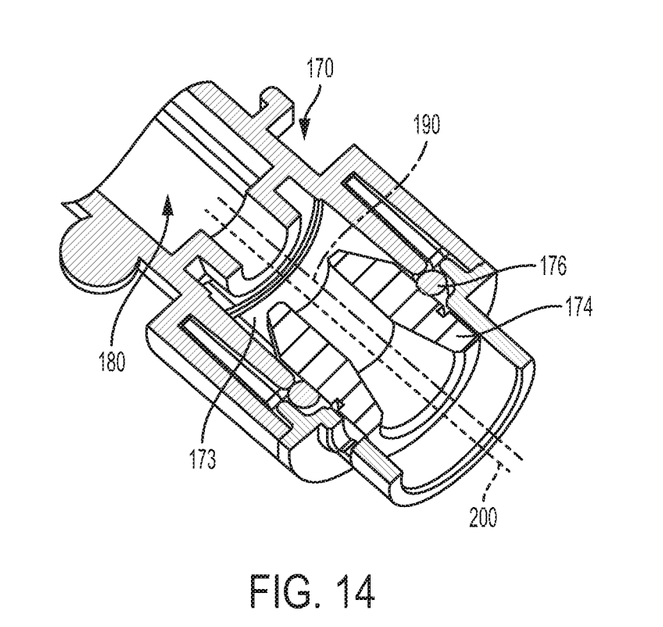
FIG. 14 is a perspective view of a cross-section of a portion of the manifold of FIG. 12.
Figure 16:
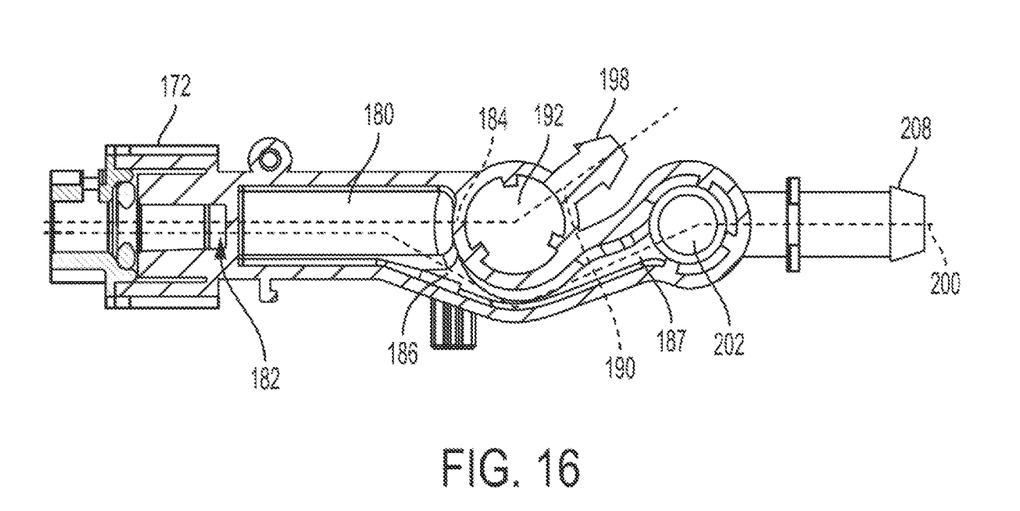
FIG. 16 is a cross-sectional bottom view of the manifold of FIG. 12.

As shown in FIGS. 14 and 16, the surgical device 100 includes a suction flow path 200 configured to provide suction therealong and an irrigation flow path 190 configured to provide irrigation therealong. The suction flow path 200 and the irrigation flow path 190 share a common path along a partial length thereof, such as in the handle 102 and the shaft 104.

Figure 13:
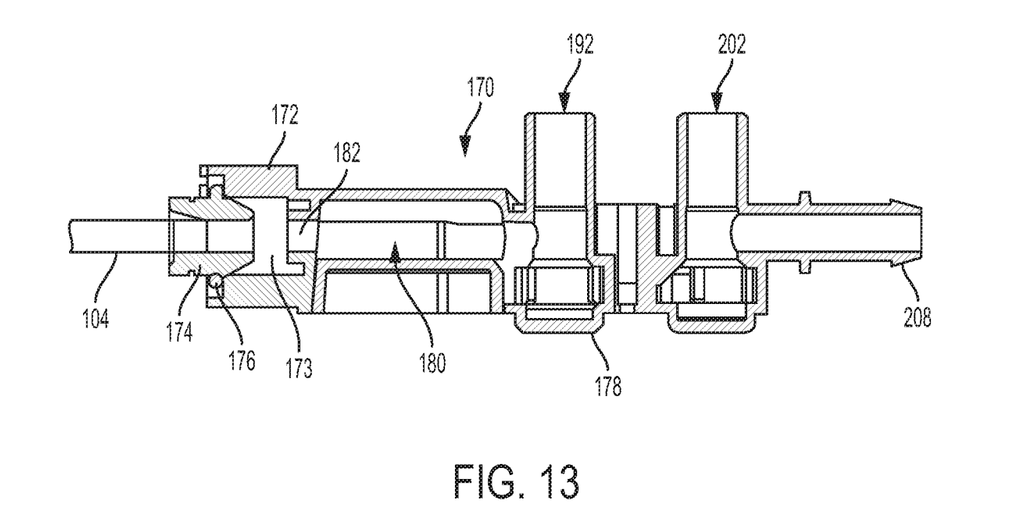
FIG. 13 is a cross-sectional side view of the manifold of FIG. 12 with an elongate shaft extending therefrom.

As illustrated in FIGS. 10-14, the handle 102 has a flow path manifold 170 that extends from a distal end 102d to a proximal end 102p of the handle 102 and is disposed in the housing 150. The manifold 170 has a distal engagement end 172, best illustrated in FIG. 11, that couples to the proximal end 104p of the elongate shaft 104 such that the shaft 104 and the flow path manifold 170 are in fluid communication. In at least some embodiments, as shown in FIG. 13, a fluid seal can be achieved between the manifold 170 and the shaft 104 through use of a barrel adaptor 174 partially disposed in an introductory chamber 173 of the distal engagement end 172 and an o-ring 176 configured to seal the distal engagement end 172 and the shaft 104. However, a variety of other engagements are possible between the manifold 170 and the shaft 104, such as interference fit, valves, plugs, etc. The introductory chamber 173 of the distal engagement end 172 is in communication with a joint chamber 180 that defines the common path of the suction flow path 200 and the irrigation flow path 190. Suction and irrigation may thus both be provided through the joint chamber 180, at different times depending on whether suction or irrigation is being applied. The joint chamber 180 has one central distal opening or orifice 182 leading to the introductory chamber 173 and the inner passageway of the elongate shaft 104 and two proximal openings 184, 186 leading to the irrigation flow path 190 and the suction flow path 200, respectively, as best illustrated in FIGS. 15 and 16.

The first proximal opening 184 in the joint chamber 180 is part of the irrigation flow path 190 and leads to an irrigation opening 192 that extends entirely through the flow path manifold 170 perpendicular to the axis L. The irrigation opening 192 is positioned in the manifold 170 such that the irrigation flow path 190 passes therethrough. An irrigation valve 194 (see FIG. 10) is positioned in the opening 192 and is configured to translate up and down in the opening 192 between an open position and a closed position. When the irrigation valve 194 is in the open position, the irrigation flow path 190 is open and fluid can flow therealong to provide irrigation through the opening 120 or the holes 122. When the irrigation valve 194 is in the closed position, the irrigation flow path 190 is closed and no fluid can flow therealong and irrigation cannot be provided through the opening 120 and the holes 122. A spring 196 biases the irrigation valve 194 to the closed position, and two o-rings 195 assist in sealing the valve 194 closed. An irrigation actuator 197, in the form of a button in this illustrated embodiment, coupled to the irrigation valve 194 and/or the housing 150 is configured to be actuated, e.g., pressed by a user, to cause irrigation. When the irrigation actuator 197 is actuated, the irrigation valve 194 is configured to move from the closed position to the open position to open the irrigation flow path 190, thereby allowing fluid flow along the irrigation flow path 190. When the irrigation actuator 197 is deactivated, e.g., the user releases the button 197, the spring 196 is configured to move the valve 194 back to the closed position. In other embodiments, a variety of closing and opening mechanisms can be used, such as seals, valves, ports, doors, etc. An irrigation port 198 extends at an angle to the axis L from the opening 192 in the irrigation flow path 190 and is configured to couple to an irrigation tube 220 that extends proximally from the port 198 and away from the handle 102. The irrigation tube 220 can terminate in an irrigation tube luer 222 that is configured to couple to an irrigation source (not shown) to provide irrigation fluid to the irritation flow path 190. The irrigation flow path 190 can thus flow from the irrigation source, through the irrigation tube 220, through the port 198 and into the joint chamber 180, along the shaft 104, and out the distal end 104d thereof to a surgical site. In at least some embodiments, the valve 194 can always be pressurized to the closed position because of pressure from the irrigation source.

The second proximal opening 186 in the joint chamber 180 is part of the suction flow path 200 and leads to a proximal suction chamber 187 (see FIGS. 15 and 16) and a suction opening 202 that extends entirely through the flow path manifold 170. The second proximal opening 186 is narrower relative to the joint chamber 180, and the proximal suction chamber 187 is wider relative to the second proximal opening 186. The suction opening 202 extends substantially perpendicular to the axis L in this illustrated embodiment. A person skilled in the art will appreciate that the suction opening 202 may not be precisely perpendicular to the axis L but nevertheless be considered to be substantially perpendicular for any of a variety of reasons, such as manufacturing tolerances and sensitivity of measurement devices. The suction opening 202 is positioned in the manifold 170 such that the suction flow path 200 passes therethrough. A suction valve 204 (see FIG. 10) is positioned in the opening 202 and is configured to translate up and down in the opening 202 between an open position and a closed position. When the suction valve 204 is in the open position, the suction flow path 200 is open and a suction force can be applied therealong. When the suction valve 204 is in the closed position, the suction flow path 200 is closed and no suction force can be applied therealong. A spring 206 biases the suction valve 204 to the closed position, and two o-rings 205 assist in sealing the valve 204 closed. A suction actuator 207, in the form of a button in this illustrated embodiment, coupled to the suction valve 204 and/or the housing 150 is configured to be actuated, e.g., pressed by a user, to cause suction. When the suction actuator 207 is actuated, the suction valve 204 is configured to move from the closed position to the open position, thereby opening the suction flow path 200 and allowing a suction force to be applied therealong. When the suction actuator 207 is deactivated, e.g., a user releases the button 207, the spring 206 is configured to bias the valve 204 back to the closed position. In other embodiments, a variety of closing and opening mechanisms can be used, such as seals, valves, ports, doors, etc. A suction port 208, which extends substantially parallel to the axis L from the opening 202 in the suction flow path 200 in this illustrated embodiment, is configured to couple to a suction tube 230 that extends proximally from the suction port 208 and away from the handle 102. A person skilled in the art will appreciate that the suction port 208 may not be precisely parallel to the axis L but nevertheless be considered to be substantially parallel for any of a variety of reasons, such as manufacturing tolerances and sensitivity of measurement devices. The suction tube 230 can terminate in a suction tube adaptor 232 that is configured to couple to a suction source (not shown) to provide a suction force to the suction flow path 200. The suction flow path 200 can thus flow from the suction source, through the suction tube 230, through the port 208 and into the joint chamber 180, along the shaft 104, and out the distal end 104d thereof to a surgical site. In some embodiments, the valve 204 can always be pressurized to the closed position because of pressure from the suction source. A valve plate 178 (see FIG. 13) can extend underneath the manifold 170 such that it blocks bottoms of the openings 192, 202 and prevents the valves 194, 204 from translating too far down. Because the second proximal opening 186 is narrower relative to the joint chamber 180, any bolus of suctioned tissue can be compressed axially relative to the flow path 200, which may reduce valve wrapping and clogging of tissue at the suction valve 204. As the proximal suction chamber 187 widens relative to the second proximal opening 186, suctioned tissue can accumulate at a proximal end of the proximal suction chamber 187, and any irrigation fluid added to the joint chamber 180 can then be suctioned through the opening 186 and the proximal suction chamber 187 to help clear the suctioned tissue through the suction valve 204 and out of the handle 102. Additionally, a velocity of the flow path 200 in the opening 186 and the chamber 187 relative to the velocity of the flow path 200 in the joint chamber 180 approximately doubles, thereby providing additional assistance in clearing any blockage or clog of tissue and/or other material from the flow path 200 and out the suction valve 204.

Figure 10:
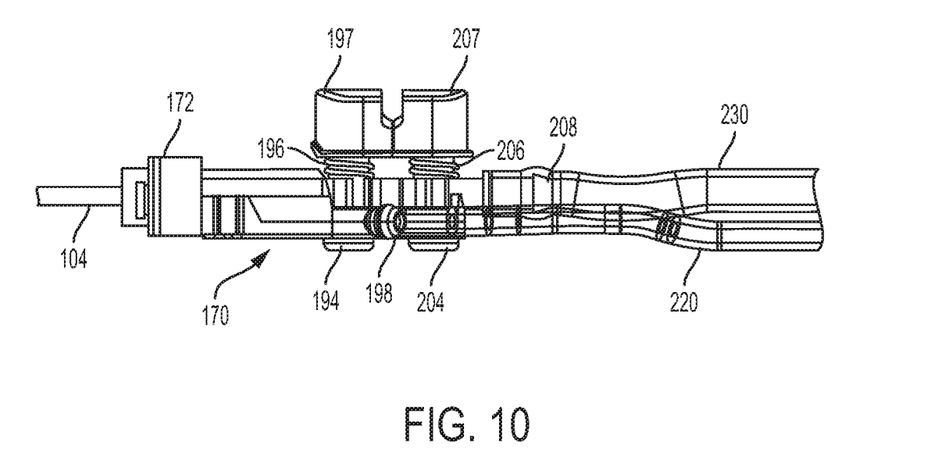
FIG. 10 is a side, internal view of a portion of the handle of FIG. 9 with select components removed.
Figure 11:
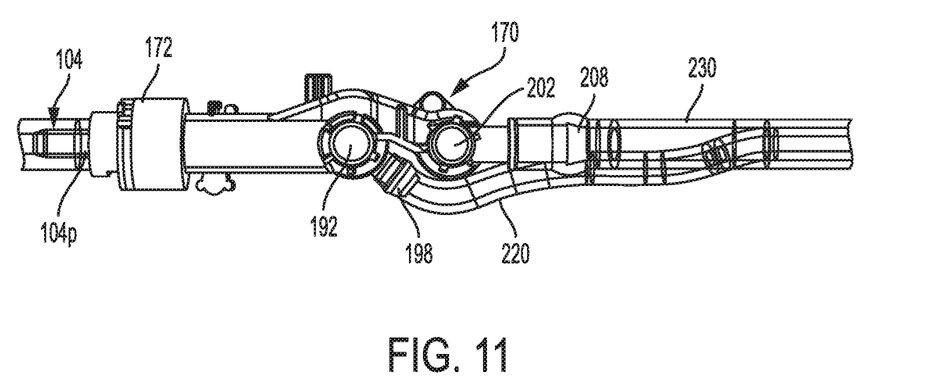
FIG. 11 is a top view of the handle of FIG. 10 with select additional components removed.
Figure 12:
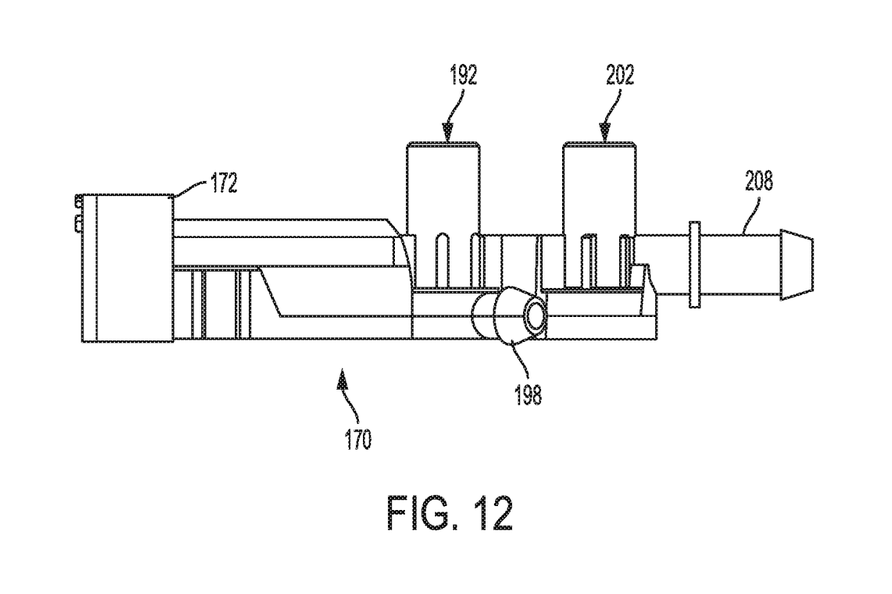
FIG. 12 is a side view of a manifold in the handle of FIG. 11.
Figure 15:
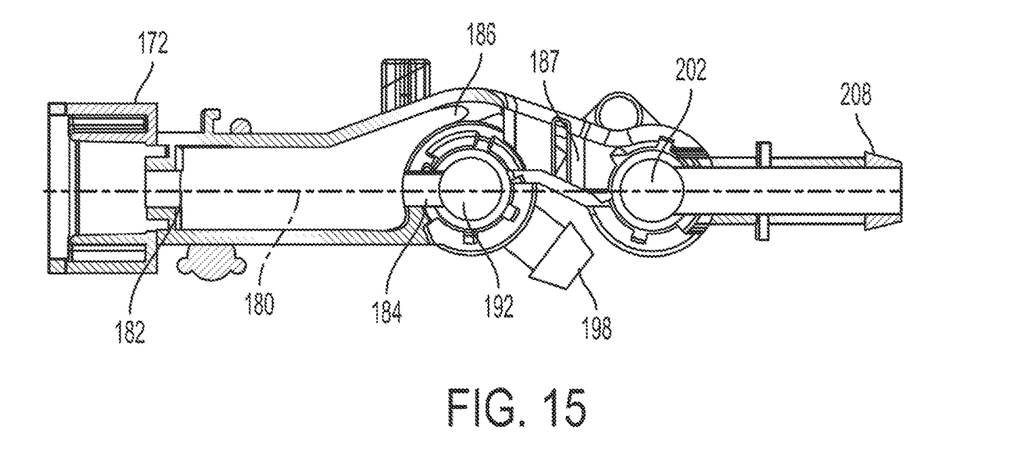
FIG. 15 is a cross-sectional top view of the manifold of FIG. 12.

As shown in FIGS. 10, 15, and 16, the irrigation valve 194 and the irrigation opening 192 are positioned approximately in line along the axis L and distal to the suction valve 204 and the suction opening 202. The irrigation flow path 190 and the suction flow path 200 are thus substantially straight along the axis L and uninterrupted from the elongate shaft 104 through the introductory chamber 173 and into the joint chamber 180, including both horizontal and vertical directions, as best illustrated in FIGS. 13 and 14. A person skilled in the art will appreciate that the paths 190, 200 may not be precisely straight but nevertheless be considered to be substantially straight for any of a variety of reasons, such as manufacturing tolerances and sensitivity of measurement devices. A person skilled in the art will also appreciate that elements, e.g., the irrigation valve 194 and the irrigation opening 192, may not be precisely in line but nevertheless be considered to be approximately in line for any of a variety of reasons, such as manufacturing tolerances and sensitivity of measurement devices. The substantially straight and uninterrupted flow paths 190, 200 may assist in providing efficient irrigation and suction to a surgical site, especially for suction that has to clear tissue and/or artifacts from the surgical site. Because the valves 194, 204 are approximately in line with each other and positioned along the axis L, tissue being suctioned from a surgical site and along the suction flow path 200 has a potential to have a high turbulence by the time the suctioned tissue reaches the suction valve 204, under which conditions the suctioned tissue can potentially wrap around the suction valve 204 and create a clog in one or both of the flow paths 190, 200 depending on the exact location and severity of the clog. However, turbulence of suctioned tissue along the suction flow path 200 and to the suction valve 204 is reduced because the flow paths 190, 200 pass through the single central distal opening 182 from the introductory chamber 173 and into the joint chamber 180 before the flow paths 190, 200 are bifurcated at the irrigation valve 194. The suction flow path 200 and any suctioned tissue may thus have a reduced turbulence as the suctioned tissue enters the suction valve 204. The joint chamber 180 may therefore allow a direct line or path to the suction valve 204 for suctioned tissue, thus reducing turbulence and reducing or eliminating clogging. Because the flow paths 190, 200 share a common path through the joint chamber 180 and the shaft 104, switching back and forth between suction and irrigation can help clear the flow paths 190, 200 and provide better flow. For example, in some embodiments a flow rate for the suction flow path 200 can be increased by approximately 33% while a flow rate of the irrigation flow path 190 can remain approximately the same or decrease by a minor amount, such as by less than 2%, when compared to other surgical devices that use two entirely separate flow paths for irrigation and suction. The increased flow rate of the suction flow path 200 may allow the device 100 to handle larger artifacts, and the at least partially combined flow path of the irrigation and the suction flow paths 190, 200 can allow fluid to be applied to any artifacts that may dry out in other circumstances.

As illustrated in FIG. 16, after leaving the joint chamber 180, the irrigation flow path 190 proceeds substantially straight into the irrigation valve 194 and the irrigation opening 192, while the suction flow path 200 curves at an angle around the irrigation valve 194 and the irrigation opening 192 to reach the suction valve 204 and the suction opening 202 positioned proximally to the irrigation valve 194 and the irrigation opening 192. In other embodiments, different orientations within the handle 102 and different components of valves, ports, tubes, etc. can be used while still maintaining a joint flow path between the irrigation flow path 190 and the suction flow path 200 along at least part of a distal portion of each of the flow paths 190, 200 thereof and independent flow paths at proximal portions thereof. In at least some embodiments, only one of the flow paths 190, 200 can be used at a time. In other embodiments, the flow paths 190, 200 can be used simultaneously to flush the joint chamber 180, the shaft 104, and/or any other portion of a common path of the flow paths 190, 200 such that any clog, tissue, artifact, etc. can be cleaned out of the common path. In other embodiments, an actuator (e.g., button, switch, knob, lever, etc.) can be provided that when actuated causes irrigation and suction, and a toggle switch or other mechanism configured to allow for dual functionality can be provided at the handle 102 to allow a user to change whether fluid is delivered or a suction force is applied. In at least some embodiments, one of the irrigation port 198 and the suction port 208 can be larger than the other. For example, the suction port 208 can be larger than the irrigation port 198 to allow for easier clearing of tissue or artifacts.

In use, the surgical device 100 can be advanced into a body of a patient, and the distal end 104d of the shaft 104 can be positioned adjacent to tissue. The irrigation actuator 197 can then be actuated, by hand or via robot or other device, to open the irrigation flow path 190 and apply irrigation to tissue. The suction actuator 207 can alternatively be actuated to open the suction flow path 200 and apply suction to tissue. Suction and irrigation can be alternately applied, or suction and/or irrigation can be applied in succession, as desired. In at least some embodiments, an end effector such as the end effector 130 can be used to apply energy to or cut tissue. For example, the actuator 152 can be actuated to apply energy to tissue.

Components of the device 100 can be laser welded together. For example, the manifold 170 can be laser welded to ensure an air-tight and/or water-tight closure and to ensure the irrigation and suction flow paths 190, 200 are kept separate outside the joint chamber 180. The manifold 170 can be made from a dark plastic that absorbs light from the laser weld and heats up to seal shut while other material is not affected by the laser weld. Many different materials can be used to form the device 100. Some examples of materials that can be used include but are not limited to various plastics such as thermoplastic, polyoxymethylene copolymer (POM), polyamides, polycarbonate, polyetherimide, polyetheretherketone, polyethylene, polylactic acid/polylactide acid (PLA), polypropylene, polystyrene, polyurethane, polyvinyl chloride (PVC), and thermoplastic elastomer. Materials having insulating properties can be used when applying energy so that the distal end 104d of the shaft 104 is insulated from the surgical site when irrigating.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and/or components, and subsequent reassembly. In particular, the device can be disassembled, and any number of the particular pieces and/or components and/or parts of the device can be selectively replaced or removed in any combination. Upon cleaning and/or replacement of particular parts, the device can be reassembled for subsequent use either at a reconditioning facility, or by a surgical team immediately prior to a surgical procedure. One skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical device, comprising:
a handle having a first chamber, a second chamber, and an opening therebetween, the handle having therein a suction flow path configured to provide suction therethrough and an irrigation flow path configured to provide irrigation therethrough, the suction flow path and the irrigation flow path sharing a common path through the first chamber, the opening, and the second chamber thereof, the handle having a second opening at a proximal end of the second chamber, a suction chamber proximal to the second opening, and a suction opening proximal to the suction chamber, the suction opening configured to accommodate a first valve, the second opening being narrower than the second chamber, the suction chamber being wider than the second opening, and a length of the suction flow path distinct from the irrigation flow path passing through the second opening and the suction chamber; and
an elongate shaft extending distally from the handle, the shaft having an inner lumen extending therethrough, the inner lumen being in communication with the suction flow path such that the inner lumen is configured to provide suction therethrough to allow matter to enter an open distal end of the shaft, and the inner lumen being in communication with the irrigation flow path such that the inner lumen is configured to provide irrigation therethrough to allow fluid to exit the open distal end of the shaft;
wherein the first chamber, the second chamber, and the opening are coaxial along a shared longitudinal axis of the handle and the shaft.

2. The device of claim 1, further comprising an actuator configured to be selectively actuated to cause the suction to be provided through the suction flow path and to cause the irrigation to be provided through the irrigation flow path.

3. The device of claim 1, further comprising the first valve at least partially disposed within the suction opening and that biases the suction flow path closed, and a second valve that biases the irrigation flow path closed.

4. The device of claim 3, further comprising a first actuator configured to be actuated to counteract the bias of the first valve to allow the suction to be provided through the suction flow path, and a second actuator configured to be actuated to counteract the bias of the second valve to allow the irrigation to be provided through the irrigation flow path.

5. The device of claim 3, wherein the first and second valves are positioned along the shared longitudinal axis of the handle and the shaft.

6. The device of claim 5, wherein the second valve is positioned distally relative to the first valve along the longitudinal axis.

7. The device of claim 6, wherein the second chamber and the common path terminate proximally at the second valve, and the suction flow path and the irrigation flow path are bifurcated at the second valve.

8. The device of claim 1, wherein the suction flow path couples to a suction port on the handle and the irrigation flow path couples to an irrigation port on the handle.

9. The device of claim 8, wherein the suction port is larger than the irrigation port.

10. The device of claim 8, wherein the suction flow path extends distally from the suction port for a first length before reaching the common path, and the irrigation flow path extends distally from the irrigation port for a second length before reaching the common path.

11. The device of claim 1, wherein the suction flow path has a length proximal to a proximal end of the common path that is configured to have a velocity greater than a velocity of the suction flow path in the common path.

12. The device of claim 1, wherein the handle has an irrigation opening, the irrigation opening and the suction opening are positioned proximal to the common path, the irrigation opening and the suction opening each extend entirely through the handle perpendicular to the shared longitudinal axis of the handle and the elongate shaft, the irrigation opening is positioned along the irrigation flow path, and the suction opening is positioned along the suction flow path.

13. The device of claim 1, wherein the suction chamber is an enclosed chamber.

14. A surgical device, comprising:
a handle having a first chamber, a second chamber, and an opening therebetween, the handle having a suction flow path configured to provide suction therethrough and an irrigation flow path configured to provide irrigation therethrough, the suction flow path and the irrigation flow path sharing a common path through the first chamber, the opening, and the second chamber thereof, the handle having a second opening at a proximal end of the second chamber, a suction chamber proximal to the second opening, and a suction opening proximal to the suction chamber, the suction opening configured to accommodate a suction valve, the second opening being narrower than the second chamber, the suction chamber being wider than the second opening, and a length of the suction flow path distinct from the irrigation flow path passing through the second opening and the suction chamber; and an elongate shaft extending distally from the handle, the shaft having an inner lumen extending therethrough, the inner lumen being in communication with the suction flow path such that the inner lumen is configured to provide suction therethrough to allow matter to enter an open distal end of the shaft, and the inner lumen being in communication with the irrigation flow path such that the inner lumen is configured to provide irrigation therethrough to allow fluid to exit the open distal end of the shaft.

15. The device of claim 14, wherein a velocity of the suction flow path through the second opening and the suction chamber is at least double a velocity of the suction flow path through the second chamber.

16. The device of claim 14, wherein the handle comprises the suction valve configured to open and close the suction flow path and an irrigation valve configured to open and close the irrigation flow path, the suction valve and the irrigation valve are positioned along a longitudinal axis of the handle and the elongate shaft, the second opening extends at least partially around the irrigation valve, the suction valve is at least partially disposed in the suction opening, and the suction chamber terminates into the suction valve and the suction opening.

17. The device of claim 16, wherein the second chamber and the common path terminate proximally at the irrigation valve, the irrigation flow path extends through the irrigation valve, and the suction flow path extends around the irrigation valve, through the second opening and the suction chamber, and through the suction valve.

18. The device of claim 14, wherein a proximal length of the suction flow path has a larger diameter than a proximal length of the irrigation flow path.

\* \* \* \* \*